(12) United States Patent
Pons et al.

(10) Patent No.: US 11,635,533 B2
(45) Date of Patent: Apr. 25, 2023

(54) RADIOLOGICAL CASSETTE WITH SHOCK ABSORBERS

(71) Applicant: TRIXELL, Moirans (FR)

(72) Inventors: Sylvain Pons, Moirans (FR); Pierre Rieuvernet, Moirans (FR)

(73) Assignee: TRIXELL, Moirans (FR)

( * ) Notice: Subject to any disclaimer, the term of this patent is extended or adjusted under 35 U.S.C. 154(b) by 0 days.

(21) Appl. No.: 17/666,406

(22) Filed: Feb. 7, 2022

(65) Prior Publication Data

US 2022/0252745 A1 Aug. 11, 2022

(30) Foreign Application Priority Data

Feb. 8, 2021 (FR) ..................................... 2101172

(51) Int. Cl.
 *G01T 1/16* (2006.01)
 *G01T 7/00* (2006.01)
 *B33Y 80/00* (2015.01)
 *A61B 6/00* (2006.01)

(52) U.S. Cl.
 CPC ................ *G01T 7/00* (2013.01); *B33Y 80/00* (2014.12); *G01T 1/16* (2013.01); *A61B 6/4283* (2013.01)

(58) Field of Classification Search
 CPC ......... G01T 7/00; G01T 1/16; G01T 1/20189; B33Y 80/00; A61B 6/4283; A61B 6/44; F16F 15/08
 See application file for complete search history.

(56) References Cited

U.S. PATENT DOCUMENTS

| 7,989,773 B2 | 8/2011 | Jadrich et al. | |
| 2008/0292059 A1* | 11/2008 | Dobrusskin | G03B 42/04 |
| | | | 378/167 |
| 2009/0122959 A1* | 5/2009 | Jadrich | G01T 1/20 |
| | | | 378/91 |
| 2010/0158197 A1* | 6/2010 | Jadrich | G01T 1/2018 |
| | | | 378/189 |
| 2015/0320373 A1* | 11/2015 | Rieuvernet | A61B 6/4405 |
| | | | 378/189 |
| 2020/0333483 A1 | 10/2020 | Suwa et al. | |

FOREIGN PATENT DOCUMENTS

| JP | 2004219705 A | * | 8/2004 |
| JP | 2009-257914 A | | 11/2009 |
| JP | 2016-33516 A | | 3/2016 |

* cited by examiner

Primary Examiner — Kiho Kim
(74) Attorney, Agent, or Firm — BakerHostetler (57) ABSTRACT

A three-dimensional part intended to cooperate with: a single-piece base comprising a first main face, a second main face, the base being delimited by four lateral faces, the base being able to support a digital detector on the first main face and an electronic circuit board, a mechanical protection housing, the base, the digital detector and the electronic circuit board being intended to be arranged in the mechanical protection housing, the housing comprising four lateral faces, a top face and a bottom face; the three-dimensional part being comprising a bottom part linked to the base and at least partially enclosing a lateral face of the base; a top part extending from the first main face of the base to the top face of the housing.

9 Claims, 3 Drawing Sheets

RADIOLOGICAL CASSETTE WITH SHOCK ABSORBERS

CROSS-REFERENCE TO RELATED APPLICATIONS

This application claims priority to foreign French patent application No. FR 2101172, filed on Feb. 8, 2021, the disclosure of which is incorporated by reference in its entirety.

FIELD OF THE INVENTION

The invention relates to the field of imaging. It can be applied to any type of imager, notably the X-ray, visible and infrared imagers. The invention is explained here in the field of X-ray medical imaging, this by way of example and with no loss of applicability to other imaging fields. The invention relates to a portable radiological cassette with shock absorbers enhancing the protection of the cassette against drops, impacts from external objects, localised or distributed pressure forces, and any stresses.

BACKGROUND

The cassette comprises a digital detector of ionising radiation that makes it possible to provide an image that is a function of the received radiation. The radiological system further comprises an ionising radiation source, such as, for example, an X-ray tube, making it possible to generate an X radiation, and a base station comprising an information processing system making it possible to synchronise the X-ray tube and the detector and also making it possible to perform image processing operations like showing the operator the image corrected of all the defects inherent to the detector and enhanced, for example by outline highlighting processing operations. An object for which an X image is wanted to be obtained is placed between the source and the detector. Such a system can be used in many applications such as, for example, medical radiology and non-destructive testing. The invention can also be implemented for other types of radiations to be detected, notably gamma radiations.

In the past, the radiological systems comprising digital sensors or image intensifying tubes were bulky and fairly immobile. The object had to be positioned with respect to the system to obtain the desired image. With the emergence of new generations of solid-state detectors, the detector has become less bulky and it has become possible to move the detector with respect to an object remaining fixed. For medical radiology, digital detectors have been used in the form of mobile cassettes that can now be placed in immediate proximity to a patient for whom an image is wanted, when the state of health of the patient prevents him or her from moving to a dedicated radiology room. These detectors now have geometrical characteristics similar to the old analogue sensors of cassette or electroluminescent screen type. They are however still more mechanically fragile than the old analogue sensors and are in particular more sensitive to the risks of breakage of the internal elements if dropped or subjected to violent impact.

The mobile cassette essentially comprises a digital detector of ionising radiation in the form of a flat panel and an electronic circuit board notably responsible for driving the digital detector. The detector and the board are arranged in a housing ensuring the mechanical protection thereof.

The cassette used in a portable system undergoes many more manipulations than in a fixed radiological system and the mechanical protection thereof must be reinforced, notably with respect to impacts to which the cassette may be subjected in its movements. More specifically, the digital detector is often produced from photosensitive components arranged in a matrix on a glass slab forming the most brittle element of the cassette. In addition to the impacts that could damage it, this slab is also sensitive to deformations, in particular by torsion.

The portable cassettes therefore have to reconcile an extreme resistance to external aggression with reduced weight and size. In fact, these portable cassettes may, in the manipulating thereof, and throughout their life, be exposed to drops, impacts from external objects, localised or distributed pressure forces, and bending stresses when the weight of a patient is exerted on a detector which is not uniformly supported. For that, the mechanical structure of the detectors must provide maximal protection of the brittle elements that are the digital detector and the electronic circuit board.

The impacts, vibrations or mechanical plays internal to the cassette result in degradations induced by these mechanical stresses. These degradations may cause the active part of the detector (photodiode matrix on a glass substrate, possibly encapsulated by a glass cover situated on top of the scintillator) to be broken, the electronic circuit boards or components placed on these boards to break or be damaged, the connectors or flexible ribbon cables intended to electrically link the various sub-assemblies to be detached or broken, and finally may cause disturbances of the radiological image caused by the vibration of the flexible connectors (so-called flexible modules) which ensure the electrical contact between the photodiode matrix and the electronic circuit boards. These degradations may occur immediately during the mechanical stressing and create an instantaneous failure. They may also originate from wear mechanisms linked to frictions or to repeated small disturbances throughout the life of the product.

To protect the sensitive parts of a cassette, several solutions are currently implemented. A first solution consists in adding layers incorporated in an external protection film. This solution does not protect the panel from external impacts due to the internal movements if dropped and tend to increase the bulk of the product which is constrained by compliance with the three-dimensional standards for radiological devices.

Another solution is to add local brackets onto the edges of the base. This solution does not protect the modules (flexible connectors) against vibrations or risks of tearing. Furthermore, the absorption capacity is very limited because of the small size of these brackets (the bulk being constrained by the standardised size of the detectors).

Finally, it is also known practice to reduce the mechanical plays. However, there is, to date, no simple solution for reducing the mechanical play other than by tightening up the dimensional tolerances of all the parts with an impact on the cost, even on the feasibility, of these parts, and difficulty of assembly.

All these solutions offer only partial protection against a restricted group of mechanical stresses (impacts, vibrations) and are not fully satisfactory.

Figure 1:
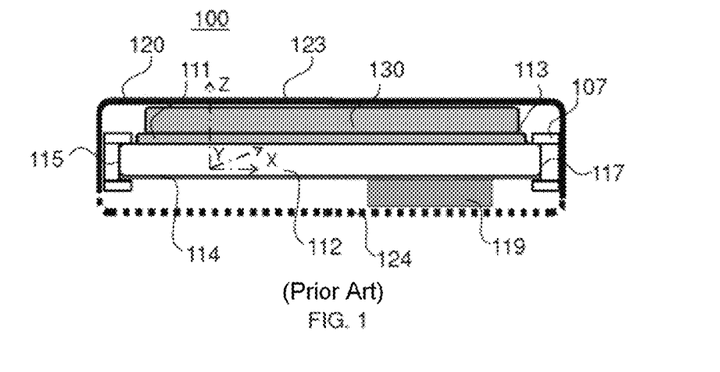
FIG. 1 schematically represents a cross-sectional view of a radiological cassette of the prior art.

FIG. 1 represents a cross-sectional view of a portable radiological cassette 100 structure known from the prior art. Conventionally, a portable radiological cassette 100 comprises:
  a digital detector 111 of ionising radiation in the form of a flat panel extending on a plane (XY);
  a base 112 comprising a first main face 113, a second main face 114, opposite the first main face 113, the base 112 being delimited by four lateral faces 115, 116 (not represented because not visible on the cross-sectional view), 117, 118, the base 112 supporting the digital detector 111 on the first main face 113;

an electronic circuit board 119 handling the management of the digital detector 111, a mechanical protection housing 120, in which are arranged the base 112, the digital detector 111 and the electronic circuit board 119, the housing 120 comprising four lateral faces, a top face 123 and a bottom face 124.

The portable radiological cassette 100 of the prior art also comprises two elements 107 positioned inside the housing 120, each element 107 being placed against a lateral face of the housing and the base. The two elements 107 act as buffers against the impacts in the lateral direction, that is to say in a plane parallel to the plane of the base (parallel to the plane (XY)). A layer of foam 130 is superposed on the axis Z at right angles to the plane (XY) on the digital detector, and positioned between the digital detector 111 and the top face 123 of the housing to insulate the detector from impacts on the axis Z. In other words, in a radiological cassette of the prior art, in order to insulate the digital detector and other brittle components of the cassette, it is necessary to have lateral impact insulation elements and an additional protection layer to absorb the impacts on the axis Z.

The shock-absorbing elements 107 whose purpose is to absorb the impacts are mounted on the housing, and the panel (base and digital detector assembly) is then placed on the housing. This arrangement does not make it possible to control the stress transmission interfaces between the shock-absorbing elements and the panel. The shock-absorbing elements are effective only in the event of stress on the edges of the detector and can therefore be considered as two-dimensional protection. The impacts on the front face are only absorbed by the layer of foam which provides very little filtering of the impacts and vibrations, and which transmits them directly to the slab without passing through the shock-absorbing elements. Such a radiological cassette 100 of the prior art is notably described in the document U.S. Pat. No. 7,989,773B2.

SUMMARY OF THE INVENTION

The invention aims to overcome all or part of the problems cited above by proposing a portable radiological cassette with shock absorbers that allow it to be protected against the occasional or repeated mechanical stresses which risk irreversibly degrading the product or affecting its performance when used in disturbed environment. The invention makes it possible to enhance the intrinsic mechanical robustness of the cassette by ensuring both the protection of the internal active part of the detector incorporated in the external housing should the detector be dropped or subjected to violent impacts, the protection of the sensitive components during the acquisition of images generating image defects given the vibrations, the reduction of the internal mechanical plays between the housing and the assembly formed by the base and the digital detector.

To this end, the subject of the invention is a portable radiological cassette comprising:
  a digital detector of ionising radiation in the form of a flat panel;
  a single-piece base comprising a first main face, a second main face, opposite the first main face, the base being delimited by four lateral faces, the base supporting the digital detector on the first main face;
  an electronic circuit board handling the management of the digital detector;
  a mechanical protection housing, in which are arranged the base, the digital detector and the electronic circuit board, the housing comprising four lateral faces, a top face and a bottom face;

the portable radiological cassette comprising at least one three-dimensional part, each of the at least one three-dimensional parts being associated with at least one of the four lateral faces of the base, each three-dimensional part comprising:
  a bottom part linked to the base and at least partially enclosing the at least one lateral face of the base with the three-dimensional part is associated;
  a top part extending from the first main face of the base to the top face of the housing;

the portable radiological cassette comprising a flexible circuit, and the bottom part of at least one of the three-dimensional parts comprises at least one recess intended to house the flexible circuit; the top part of at least one of the three-dimensional parts comprising at least one aperture on an axis substantially at right angles to the lateral face of the base with which the three-dimensional part is associated;

the portable radiological cassette comprising a comb comprising a branch extending substantially parallel to the first main face of the base and in contact on the bottom part of the three-dimensional part, the branch being provided with at least one tooth extending substantially at right angles to the branch, the at least one tooth being configured to cooperate with the three-dimensional part so as to immobilise the branch against the flexible circuit.

Advantageously, the bottom part of at least one of the three-dimensional parts partially encloses a lateral face adjacent to the lateral face of the base with which the three-dimensional part is associated.

Advantageously, the at least one tooth is inserted into the aperture of the top part of the three-dimensional part and configured to block the comb in translation in a plane substantially parallel to the base.

Advantageously, the top part of at least one of the three-dimensional parts is terminated by a form complementing the top face of the housing.

Advantageously, the at least one three-dimensional part is made of elastomer, of polyurethane, of thermoplastic elastomer, of polyamide and/or of polyester.

Advantageously, the bottom part of the at least one three-dimensional part is glued to the base.

The invention relates also to a three-dimensional part intended to cooperate with:
  a single-piece base comprising a first main face, a second main face, opposite the first main face, the base being delimited by four lateral faces, the base being able to support a digital detector on the first main face and an electronic circuit board,
  a mechanical protection housing, the base, the digital detector and the electronic circuit board being intended to be arranged in the mechanical protection housing, the housing comprising four lateral faces, a top face and a bottom face;
  the three-dimensional part comprising:
  a bottom part linked to the base and at least partially enclosing a lateral face of the base;
  a top part extending from the first main face of the base to the top face of the housing.

The invention relates also to a computer program product, said computer program comprising computer-executable instructions which, when they are executed by a processor, cause the processor to control an additive manufacturing device to manufacture the three-dimensional part according to the invention.

The invention relates also to a method for manufacturing the three-dimensional part according to the invention by additive manufacturing, the method comprising: obtaining an electronic file representing a geometry of a product in which the product is the three-dimensional part; and controlling an additive manufacturing device to manufacture, over one or more additive manufacturing steps, the product according to the geometry specified in the electronic file.

BRIEF DESCRIPTION OF THE DRAWINGS

The invention will be better understood and other advantages will emerge on reading the detailed description of an embodiment given as an example, the description being illustrated by the attached drawing in which.

In these figures, in the interests of clarity, the scales are not observed. Moreover, the same elements will bear the same references in the various figures.

DETAILED DESCRIPTION

FIG. 1 schematically represents a cross-sectional view of a radiological cassette 100 of the prior art and which has already been presented in the introduction.

Figure 2:
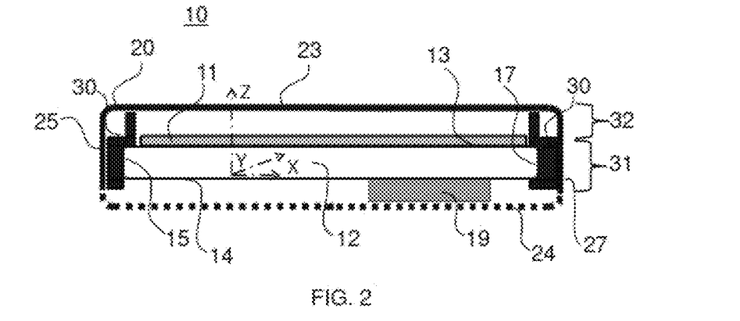
FIG. 2 schematically represents a cross-sectional view of a part of a radiological cassette according to the invention.

FIG. 2 schematically represents a cross-sectional view of a part of a radiological cassette 10 according to the invention. The portable radiological cassette 10 comprises a digital detector 11 of ionising radiation in the form of a flat panel. The cassette 10 comprises a single-piece base 12 comprising a first main face 13, a second main face 14, opposite the first main face 13, the base 12 being delimited by four lateral faces 15, 16, 17, 18 (the face 16 is the rear lateral face not visible in this cross-sectional view and the face 18 is the front lateral face not visible in this cross-sectional view), the base 12 supporting the digital detector 11 on the first main face 13. The base extends on a plane (XY). The digital detector is therefore superposed on the axis Z at right angles to the plane (XY) on the base 12. The cassette 10 further comprises at least one electronic circuit board 19 ensuring the handling of the management of the digital detector 11. The electronic circuit board 19 is generally positioned on the second main face 14 of the base, but it can also be positioned on the first main face 13 or in another location of the cassette 10. Finally, the cassette 10 comprises a mechanical protection housing 20, in which are arranged the base 12, the digital detector 11 and the electronic circuit board 19. The housing 20 comprises four lateral faces 25, 26, 27, 28 (the face 26 is the rear lateral face not visible in this cross-sectional view and the face 28 is the front lateral face not visible in this cross-sectional view), a top face 23 and a bottom face 24. According to the invention, the portable radiological cassette 10 comprises at least one three-dimensional part 30 (hereinbelow, by way of example and in a nonlimiting manner, several three-dimensional parts will be considered), each of the three-dimensional parts 30 being associated with one of the four lateral faces 15, 16, 17, 18 of the base 12. Each three-dimensional part 30 comprises a bottom part 31 linked to the base 12 and at least partially enclosing the lateral face 15, 16, 17, 18 of the base 12 with which the three-dimensional part 30 is associated. As detailed hereinbelow, the bottom part 31 linked to the base 12 can at least partially enclose at least one lateral face of the base 12 with which the three-dimensional part 30 is associated. It can for example enclose two of them. And each three-dimensional part 30 comprises a top part 32 extending from the first main face 13 of the base 12 to the top face 23 of the housing 20.

The three-dimensional parts can be likened to three-dimensional shock absorbers in the three dimensions X, Y, Z.

The three-dimensional parts 30 can be made of elastomer, of polyurethane, of thermoplastic elastomer, of polyamide and/or of polyester or any other material having similar mechanical characteristics.

The three-dimensional parts guarantee the absorptions of forces between the panel (assembly formed by the base 12 and the digital detector 11) and the housing 20 in the three directions. The three-dimensional parts make it possible to filter the accelerations transmitted to the X imaging technology (panel) if the detector is dropped.

The three-dimensional parts are designed such that the heightwise wedging on the axis Z is produced between the modules. That avoids the transmission of the external vibrations to the modules. That filters the transmission of the vibrations to the modules and allows a significant reduction in so-called "microphony" defects.

Furthermore, the properties of the material used, preferentially but in a nonlimiting manner made of elastomer, also make it possible to limit the internal plays between the panel and the housing. The result thereof is a limitation of the internal movements which would be the source of defects when using the product (notably electrical disconnections, abrasion).

By virtue of the three-dimensional parts, the positioning of the detection elements with respect to the external marking is guaranteed more accurately.

The possibilities in the choice of material for these parts make it possible to consider injection moulding manufacturing methods, and therefore make it possible to produce these parts with low production costs. Other manufacturing methods, for example additive manufacturing, can also be considered, as discussed hereinbelow.

The three-dimensional parts serve to wedge the base with respect to the housing both in the plane XY and also heightwise Z. A single part makes it possible to guarantee isolation from impacts on the three axes X, Y, Z. The advantages which devolve therefrom are great mechanical robustness despite the cassette being dropped, vibrations during image acquisition, abrupt handling by the user. The three-dimensional parts ensure protection against the occasional or repeated mechanical stresses which risk irreversibly degrading the product or affecting its performance when used in a disturbed environment. Furthermore, the three-dimensional parts add no notable extra cost to the detector.

The internal active part of the digital detectors is composed of brittle parts which risk breaking if the cassette is dropped or subjected to violent impact. The active core of the cassette (panel+electronic circuit boards) can undergo significant deformations under the effect of the shockwaves created by a drop or a violent lateral impact on the outer enclosure.

A flexible or elastic hold is nevertheless necessary to ensure the positioning of the sensitive image zone with respect to the outer mechanical reference of the product.

These flat digital detectors are also sensitive to mechanical disturbances originating from the outside environment (impacts, vibrations) in the routine use thereof. Without being destructive to the product, these mechanical disturbances are likely to create visible artefacts in the radiological images, most often in the form of more or less dark lines which appear in the images and greatly degrade the quality thereof.

The invention therefore makes it possible to avoid breaking the internal active part if the product is dropped (drop heights being typically from 80 cm to 120 cm), and avoid the disturbances induced in the images.

In one embodiment (visible in the right part of FIG. 2), the bottom part 31 linked to the base 12 extends from the second main face 14 of the base 12 to the first main face 13 of the base and in contact with the lateral face of the housing 20 facing it. In this embodiment, the bottom part 31 holds a portion of the base 12 like a vice.

In another embodiment (visible on the left part of FIG. 2), the bottom part 31 linked to the base 12 extends from the lateral face of the base 12 to the first main face 13 of the base and in contact with the lateral face 20 opposite. In this embodiment, the bottom part 31 clamps a portion of the base 12.

The three-dimensional parts according to the invention can also take other forms, for example brackets, with a bottom part linked to the base.

The bottom part 31 of the three-dimensional parts 30 is preferentially glued to the base 12. It can also be clipped or fixed to the base by any other suitable fixing means.

Figure 3:
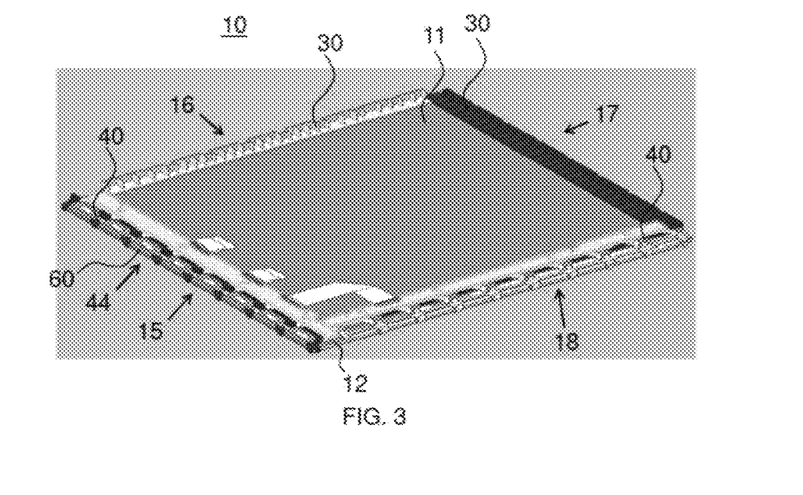
FIG. 3 schematically represents a view of a part of the portable digital cassette according to the invention without the housing.

FIG. 3 schematically represents a view of a part of the portable digital cassette 10 according to the invention without the mechanical protection housing 20.

The radiological cassette 10 can comprise first three-dimensional parts 30 and/or second three-dimensional parts 40. The first three-dimensional parts 30 and the second three-dimensional parts 40 comprise a bottom part 31 and a top part 32. The first three-dimensional parts 30 have their top part 32 which extends from their bottom part 31 and to a certain height on the axis Z corresponding to the height under the housing, that is to say under the face 23 of the housing 20. The aim of the top part is to absorb the forces on Z.

The second three-dimensional parts 40 are distinguished from the first three-dimensional parts 30 by their bottom part 41. The portable radiological cassette 10 generally comprises one flexible circuit 60 (or several thereof) that can contain an electronic component. The bottom part 41 of the three-dimensional parts 40 comprises at least one recess 44 intended to house the flexible circuit 60.

Figure 4:
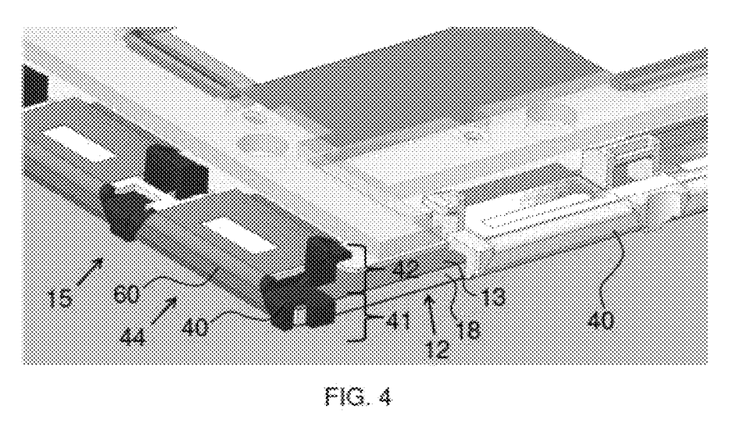
FIG. 4 schematically represents an enlargement of the view of the portable digital cassette according to the invention without the housing presented in FIG. 3.

FIG. 4 schematically represents an enlargement of the view of the portable digital cassette 10 according to the invention without the housing 20 presented in FIG. 3. As will be seen a little later in detail, the flexible circuit 60 is positioned in the recess 44 of the bottom part 41. This positioning allows the flexible circuit to be wedged well in position. In the case of a lateral impact, the bottom part 41 can be crushed slightly to absorb the forces.

The top part 42 of at least one of the three-dimensional parts 40 can be terminated by a form complementing the top face 23 of the housing 20. In other words, the top part 42 is terminated in its top part by a combination of recesses and/or protuberances of a form complementing the form of the face 23 to closely follow the internal forms of the housing 20.

The bottom part 41 of at least one of the three-dimensional parts 40 (just as is also true for the bottom part 31 of a part 30) can partially enclose a lateral face 18 adjacent to the lateral face 15 of the base 12 with which the three-dimensional part is associated. In other words, the bottom part of the three-dimensional part can enclose a corner of the base.

Figure 5:
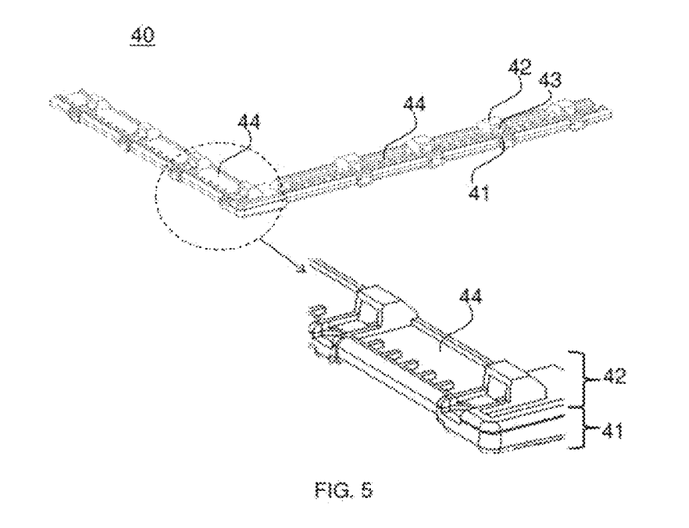
FIG. 5 represents a three-dimensional part for a portable digital cassette according to the invention.

FIG. 5 represents a three-dimensional part 40 for a portable digital cassette 10 according to the invention. As explained previously, the three-dimensional part 40 is intended to cooperate with:
- a single-piece base 12 comprising a first main face 13, a second main face 14, opposite the first main face 13, the base 12 being delimited by four lateral faces 15, 16, 17, 18, the base 12 being able to support a digital detector 11 on the first main face 13 and an electronic circuit board,
- a mechanical protection housing 20, the base 12, the digital detector 11 and the electronic circuit board 19 being intended to be arranged in the mechanical protection housing 20, the housing 20 comprising four lateral faces 25, 26, 27, 28, a top face 23 and a bottom face 24.

According to the invention, the three-dimensional part 40 comprises a bottom part 41 linked to the base 12 and at least partially enclosing a lateral face 15, 16, 17, 18 of the base 12; and a top part 42 extending from the first main face 13 of the base 12 to the top face 23 of the housing 20.

In this figure, the recess 44 of the bottom part 41 of the three-dimensional parts 40 intended to house the flexible circuit 60 is highlighted.

It can be noted that the three-dimensional part can be associated with a lateral face of the base (as presented in FIGS. 3 and 4) or else can be associated with more than two lateral faces, for example two, as can be seen in FIG. 5. In this latter variant, the bottom part 41 extends along two lateral edges of the base 12. Such a three-dimensional part, in addition to covering two lateral faces of the base, makes it possible to correctly position the elements with respect to the housing. Also, a single three-dimensional part is sufficient to absorb the impacts in three directions (X and Y by the bottom parts 41 and Z by the top parts 42).

The top part 42 of at least one of the three-dimensional parts 40 comprises at least one aperture 43 on an axis substantially at right angles to the lateral face of the base 12 with which the three-dimensional part 40 is associated. The role of this aperture 43 is explained by means of the next figure.

Figure 6:
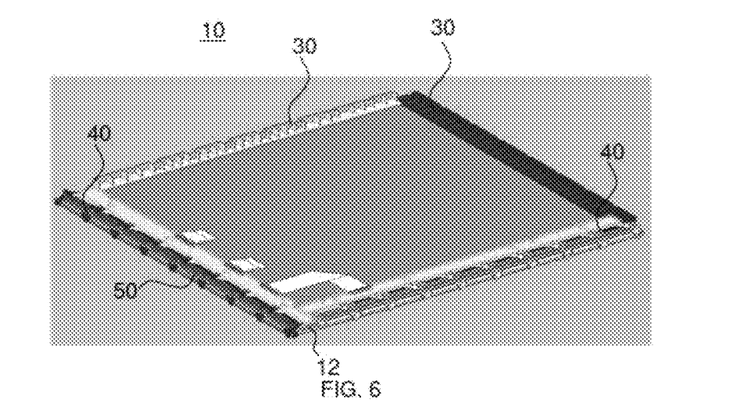
FIG. 6 schematically represents a view of another embodiment of the portable digital cassette according to the invention without the housing.

FIG. 6 schematically represents a view of another embodiment of the portable digital cassette 10 according to the invention without the housing 20, linked with the second three-dimensional parts 40. The view presented in FIG. 6 is identical to the view presented in FIG. 3. In this view, the cassette 10 further comprises a comb 50 which is intended to cooperate with a three-dimensional part 40, as detailed in FIG. 7, to ensure that the flexible circuit 60 is held in position in the recess and to press it against the bottom part 41 of the three-dimensional part.

Figure 7:
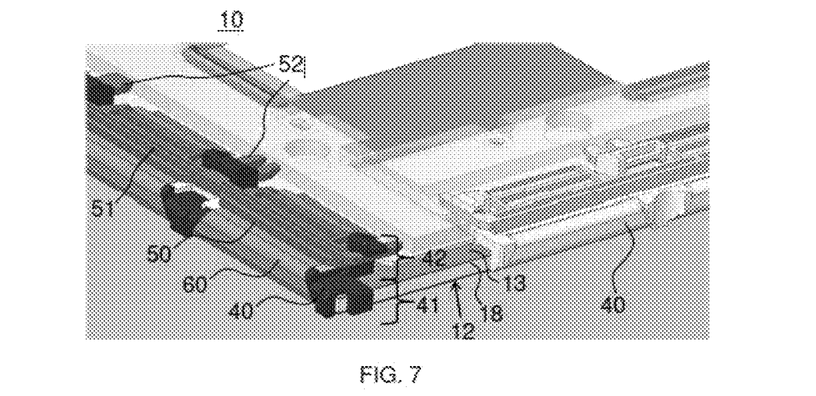
FIG. 7 schematically represents an enlargement of the view of the portable digital cassette according to the invention without the housing presented in FIG. 6.

FIG. 7 schematically represents an enlargement of the view of the portable digital cassette 10 according to the invention without the housing 20 presented in FIG. 6. As can be seen in a little more detail, the cassette 10 comprises a comb 50 comprising a branch 51 extending substantially parallel to the first main face 13 of the base 12 and in contact on the bottom part 41 of the three-dimensional part 40, the branch 51 being provided with at least one tooth 52 extending substantially at right angles to the branch 51, the at least one tooth 52 being configured to cooperate with the three-dimensional part 40 so as to immobilise the branch 51 against the flexible circuit (60).

The at least one tooth 52 is inserted into the aperture 43 of the top part 42 of the three-dimensional part 40 and configured to block the comb 50 in translation in a plane substantially parallel to the base 12. The comb 50 is blocked in translation in the plane XY and, by the insertion of the teeth 52 into the apertures 43, on the axis Z. The comb 50 presses the flexible circuits 60 towards the base, against the bottom part of the three-dimensional part 40. The comb guarantees the correct positioning of the flexible circuits 60 which must absolutely be held very accurately with respect to the base. It should also be noted that the bottom part 41 of the part 40 can extend very slightly (by the order of a few tenths of a millimetre) beyond the flexible circuit. In other words, the lateral thickness of the bottom part 41 is greater than the thickness of the flexible circuit which can possibly extend beyond the base at the lateral face of the base. This configuration contributes to the holding of the flexible circuit in position even in the case of impacts: the three-dimensional part is sufficiently flexible to be crushed and ensure a uniform effect over the entire length of the three-dimensional part.

In the above, only the comb 50 has been mentioned. The invention can be applied with a single comb, but it also advantageously includes several combs, as represented in FIG. 7.

Thus, in addition to their three-dimensional shock-absorbing role, the three-dimensional part 40 allows the incorporation of a comb, a part for holding modules/flexible circuits, mechanically insulated from the housing. That contributes to the improved filtering of the external vibrations to the modules/flexible circuits.

The invention relies on the three-dimensional part capable of absorbing the impacts and vibrations in all the directions X, Y, Z and thus protecting the detectors against the risks of breakage. The three-dimensional part constitutes a mechanical filter between the mechanical protection housing and the active core of the detector. Its elastic structure makes it possible to position the sensitive image zone of the digital detector with respect to the external mechanical reference.

Another advantage of the invention is that this three-dimensional part is removable and allows for easy repair or exchange of the panel and of the electronic circuit boards. Finally, this three-dimensional part contributes to the rigidity of the panel by limiting the uncontrolled local bends upon the propagation of the shockwaves created by a lateral impact.

The invention relates also to a computer program product, said computer program comprising computer-executable instructions which, when they are executed by a processor, cause the processor to control an additive manufacturing device to manufacture the three-dimensional part 30 or 40 as described previously.

Figure 8:
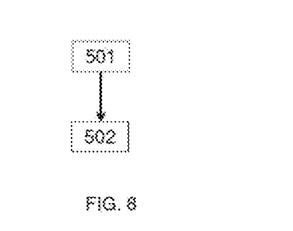
FIG. 8 schematically represents the steps of a method for manufacturing the three-dimensional part according to the invention by additive manufacturing.

FIG. 8 schematically represents the steps of a method for manufacturing the three-dimensional part according to the invention by additive manufacturing. The method for manufacturing the three-dimensional part 30, 40 by additive manufacturing comprises a step 501 which consists in obtaining an electronic file representing a geometry of a product in which the product is the three-dimensional part 30 or 40; and a step 502 of controlling an additive manufacturing device to manufacture, over one or more additive manufacturing steps, the product according to the geometry specified in the electronic file.

Examples according to the disclosure can be formed by using an additive manufacturing method. A common example of additive manufacturing is 3D printing; however, other additive manufacturing methods are available. Fast-prototyping or fast manufacturing are also terms which can be used to describe additive manufacturing methods. As used here, "additive manufacturing" refers generally to manufacturing methods in which successive layers of materials are disposed one on top of the other to "construct", layer by layer, or "additively manufacture", a three-dimensional component. This is compared to certain subtractive manufacturing methods (such as milling or drilling), in which the material is successively removed to manufacture the part. The successive layers generally fuse together to form a monolithic component which can have a variety of incorporated sub-components. In particular, the manufacturing method can allow an example of the disclosure to be formed fully and include a variety of characteristics which are not possible when using prior manufacturing methods. The additive manufacturing methods described here make it possible to manufacture to any size and form that are appropriate with various characteristics which may not have been possible by using prior manufacturing methods. Additive manufacturing can create complex geometries without using any type of tools, moulds or rigs, and with little or no waste. Instead of machining components from solid billets of plastic or of metal, a major part of which is cut away and discarded, the only material used in additive manufacturing is that which is necessary to fashion the part.

The additive manufacturing techniques that are appropriate according to the present disclosure comprise, for example, Fused Deposition Modelling (FDM), Selective Laser Sintering (SLS), 3D printing such as by inkjet and laser jet, stereolithography (SLA), Direct Selective Laser Sintering (Stereolithography or DSLS), Electron Beam Sintering (EBS), Electron Beam Melting (EBM), Laser-Engineered Net Shaping (LENS), Electron Beam Additive Manufacturing (EBAM), Laser Net Shape Manufacturing (LNSM), Direct Metal Deposition (DMD), Digital Light Processing (DLP), Continuous Digital Light Processing (CDLP), Direct Selective Laser Melting (DSLM), Selective Laser Melting (SLM), Direct Metal Laser Melting (DMLM), Direct Metal Laser Sintering (DMLS), Material Jetting (MJ), NanoParticle Jetting (NPJ), Drop On Demand (DOD), Binder Jetting (BJ), Multi Jet Fusion (MJF), Laminated Object Manufacturing (LOM) and other known methods. The additive manufacturing methods described here can be used to form components by using any appropriate material. For example, the material can be plastic, composite, polymer, epoxy, photopolymer resin or any other appropriate material which can be in solid, liquid, powder, sheet or thread form or any other appropriate form, or combinations thereof. More specifically, according to exemplary embodiments of the present subject matter, the components manufactured additively described here can be formed partly or wholly, or in a certain combination of materials. These materials are examples of materials that are appropriate for use in additive manufacturing methods which can be appropriate for the manufacturing examples described here.

As indicated above, the additive manufacturing method described allows a single component to be formed from several materials. Thus, the examples described here can be formed from any appropriate mixture of the above material. For example, a component may comprise several layers, segments or parts which are formed by using different materials, methods and/or on different additive manufacturing machines. That way, components can be constructed which have different materials and material properties to meet the requirements of any particular application. Furthermore, although the components described here are entirely constructed by additive manufacturing methods, it should be noted that, in alternative embodiments, all or part of these components can be formed by moulding, machining and/or any other appropriate manufacturing method. Indeed, any appropriate combination of materials and of manufacturing methods can be used to form these components. The additive manufacturing methods generally manufacture components on the basis of three-dimensional (3D) information, for example a three-dimensional computer model (or design file), of the component. Consequently, the examples described here comprise not only products or components as described here, but also methods for manufacturing such products or components via the additive manufacturing and software, firmware or computer hardware to control the manufacturing of such products via the additive manufacturing.

The structure of one or more parts of the product can be represented digitally in the form of a design file. A design file, or computer-aided design (CAD) file, is a configuration file which codes one or more surface or volumetric configurations of the form of the product. In other words, a design file represents the geometrical disposition or the form of the product. The design files can be in any file format that is now known or to be developed. For example, the design files can be in the stereolithography format or "Standard Tessellation Language" (.stl) which was created for the CAD stereolithography programs of 3D systems, or in the Additive Manufacturing File (.amf) format, a format promoted by the standards-based American Society for Mechanical Engineers (ASME) and which is based on an extensible markup language (XML) designed to allow any CAD software to describe the form and the composition of any three-dimensional object to be manufactured on any additive manufacturing printer. Other examples of design file formats include AutoCAD (.dwg) files, Blender (.blend) files, Parasolid (.x_t) files, 3D Manufacturing Format (0.3mf) files, Autodesk (3ds) files, Collada (.dae) files and Wavefront (.obj) files, although many other file formats exist. The design files can be produced using modelling software (for example, CAD modelling) and/or by scanning the surface of a product to measure the configuration of the surface of the product.

Once obtained, a design file can be converted into a set of computer-executable instructions which, once executed by a processor, cause the processor to control an additive manufacturing device to produce a product according to the geometrical disposition specified in the design file. The conversion can convert the design file into slices or layers which must be formed sequentially by the additive manufacturing device. The instructions (also known as geometrical code or "code G") can be calibrated according to the specific additive manufacturing device and can specify the precise placement and the quantity of the material to form each step of the manufacturing process. As discussed above, the formation can be done by deposition, by sintering or by any other form of additive manufacturing method. The code or the instructions can be translated into different formats, converted into a set of data signals and transmitted, received in the form of a set of data signals and converted into code, stored, etc., if necessary. The instructions can be an input of the additive manufacturing system and can originate from the parts designer, from an intellectual property (IP) provider, from a design company, from the operator or from the owner of the additive manufacturing system, or from other sources. An additive manufacturing system can execute the instructions to manufacture the product by using any one of the technologies or methods described here. The design files or the computer-executable instructions can be stored on a computer-readable storage medium (transient or not) (for example, memory, storage system, etc.) storing a code, or computer-readable instructions, representative of the product to be manufactured. As noted, the code or the computer-readable instructions define the product which can be used to physically generate the object, upon the execution of the code or of the instructions by an additive manufacturing system. For example, the instructions can include an accurately defined 3D model of the product and can be generated from one of many well-known computer-aided design (CAD) software systems such as AutoCAD®, TurboCAD®, DesignCAD 3D Max, etc. As a variant, a model or prototype of the component can be scanned to determine the three-dimensional information of the component.

Consequently, by controlling an additive manufacturing device according to the computer-executable instructions, the additive manufacturing device can be charged with printing one or more parts of the product. Those can be printed in assembled or non-assembled form. For example, different sections of the product can be printed separately (in the form of a kit of unassembled parts), then assembled. As a variant, and preferentially, the various parts can be printed in assembled form. In light of the above, the embodiments comprise additive manufacturing-based manufacturing methods. That includes the steps of obtaining a design file representing the product and the instruction of an additive manufacturing device to manufacture the product in an assembled or non-assembled form according to the design file. The additive manufacturing device can comprise a processor which is configured to automatically convert the design file into computer-executable instructions to control the manufacturing of the product. In these embodiments, the design file itself can automatically provoke the production of the product once entered into the additive manufacturing device. Consequently, in this embodiment, the design file itself can be considered as computer-executable instructions which cause the additive manufacturing device to manufacture the product. As a variant, the design file can be converted into instructions by an external computing system, the resulting computer-executable instructions being supplied to the additive manufacturing device. Given the above, the design and the manufacturing of the implementations of the subject and the operations described in this specification can be performed using digital electronic circuits, or in software, firmware or computer hardware, including the structures described in this specification and the structural equivalents thereof, or in combinations of one or more thereof. For example, the hardware can include processors, microprocessors, electronic circuits, electronic components, integrated circuits, etc. The implementations of the subject described in this specification can be realised using one or more computer programs, that is to say one or more modules of computer program instructions, coded on a computer storage medium for execution by, or to control the operation of, a data processing device. As a variant or in addition, the program instructions can be coded on an artificially generated propagated signal, for example, a machine-generated electrical, optical or electromagnetic signal for coding the information to be transmitted to an appropriate receiving device for execution by a data processing device. A computer storage medium can be, or be included in, a computer-readable storage device, a computer-readable storage substrate, a matrix or a random or serial access memory device, or a combination of one or more thereof. Furthermore, although a computer storage medium is not a propagated signal, a computer storage medium can be a source or a destination of computer program instructions coded in an artificially generated propagated signal. The computer storage medium can also be, or be included in, one or more separate physical components or media (for example, several CDs, discs or other storage devices). Although the additive manufacturing technology is described here as allowing the manufacturing of complex objects by constructing objects point by point or layer by layer, typically in a vertical direction, other manufacturing methods are possible and within the scope of the present subject matter. For example, although the description here refers to the addition of material to form successive layers, the person skilled in the art will appreciate that the methods and structures described here can be put into practice with any additive manufacturing technique or other manufacturing technology. Injection moulding or manufacturing by low-pressure elastomer casting can also be cited.

The invention applies mainly to the production of image sensors for radiology and more particularly to the sensors of "portable" type which are regularly subjected to impacts or likely to drop when they are handled. However, the person skilled in the art will understand that the invention can be applied to any device comprising, instead of the digital detector, a brittle electronic element linked by flexible modules linked to another electronic element, such as displays, touch or non-touch screens.

The invention claimed is:

1. A portable radiological cassette comprising:
   a digital detector of ionising radiation in the form of a flat panel;
   a single-piece base comprising a first main face, a second main face, opposite the first main face, the base being delimited by four lateral faces, the base supporting the digital detector on the first main face;
   an electronic circuit board handling the management of the digital detector;
   a mechanical protection housing, wherein are arranged the base, the digital detector and the electronic circuit board, the housing comprising four lateral faces, a top face and a bottom face;
   wherein the portable radiological cassette comprises at least one three-dimensional part, each of the at least one three-dimensional parts being associated with at least one of the four lateral faces of the base, each three-dimensional part comprising:
   a bottom part linked to the base and at least partially enclosing the at least one lateral face of the base with which the three-dimensional part is associated;
   a top part extending from the first main face of the base to the top face of the housing;
   and in that the portable radiological cassette comprises a flexible circuit;
   the bottom part of at least one of the three-dimensional parts comprising at least one recess intended to house the flexible circuit;
   the top part of at least one of the three-dimensional parts comprising at least one aperture on an axis substantially at right angles to the lateral face of the base with which the three-dimensional part is associated;
   and in that the portable radiological cassette comprises a comb comprising a branch extending substantially parallel to the first main face of the base and in contact on the bottom part of the three-dimensional part, the branch being provided with at least one tooth extending substantially at right angles to the branch, the at least one tooth being configured to cooperate with the three-dimensional part so as to immobilise the branch against the flexible circuit.

2. The portable radiological cassette according to claim 1, wherein the bottom part of at least one of the three-dimensional parts partially encloses a lateral face adjacent to the lateral face of the base with which the three-dimensional part is associated.

3. The portable radiological cassette according to claim 1, wherein the at least one tooth is inserted into the aperture of the top part of the three-dimensional part and configured to block the comb in translation in a plane substantially parallel to the base.

4. The portable radiological cassette according to claim 1, wherein the top part of at least one of the three-dimensional parts is terminated by a form complementing the top face of the housing.

5. The portable radiological cassette according to claim 1, wherein the at least one three-dimensional part is made of elastomer, of polyurethane, of thermoplastic elastomer, of polyamide and/or of polyester.

6. The portable radiological cassette according to claim 1, wherein the bottom part of the at least one three-dimensional part is glued to the base.

7. A three-dimensional part intended to cooperate with:
   a single-piece base comprising a first main face, a second main face, opposite the first main face, the base being delimited by four lateral faces, the base being able to support a digital detector on the first main face and an electronic circuit board,
   a mechanical protection housing, the base, the digital detector and the electronic circuit board being intended to be arranged in the mechanical protection housing, the housing comprising four lateral faces, a top face and a bottom face;
   the three-dimensional part being comprising:
   a bottom part linked to the base and at least partially enclosing a lateral face of the base;
   a top part extending from the first main face of the base to the top face of the housing,
   the bottom part comprising at least one recess intended to house a flexible circuit;
   the top part comprising at least one aperture on an axis substantially at right angles to a lateral face of the base with which the three-dimensional part is intended to be associated.

8. A computer program product, said computer program comprising computer-executable instructions which, when they are executed by a processor, cause the processor to control an additive manufacturing device to manufacture the three-dimensional part according to claim 7.

9. A method for manufacturing the three-dimensional part according to claim 7 by additive manufacturing, the method comprising: obtaining (step 501) an electronic file representing a geometry of a product wherein the product is the three-dimensional part; and controlling (step 502) an additive manufacturing device to manufacture, over one or more additive manufacturing steps, the product according to the geometry specified in the electronic file.

\* \* \* \* \*